US012558163B2

(12) United States Patent
Alexander et al.

(10) Patent No.: US 12,558,163 B2
(45) Date of Patent: Feb. 24, 2026

(54) METHOD FOR MEDICAL IMAGE RECONSTRUCTION

(71) Applicant: Hoth Intelligence, Inc., Philadelphia, PA (US)

(72) Inventors: Tyler Alexander, Philadelphia, PA (US); Jonathan Cohen, Pittsburgh, PA (US); Andrew Beacham, New York, NY (US); Remi Prince, New York, NY (US); Andrew Conklin, Philadelphia, PA (US)

(73) Assignee: Hoth Intelligence, Inc., Philadelphia, PA (US)

( * ) Notice: Subject to any disclaimer, the term of this patent is extended or adjusted under 35 U.S.C. 154(b) by 754 days.

(21) Appl. No.: 17/719,043

(22) Filed: Apr. 12, 2022

(65) Prior Publication Data

US 2023/0116175 A1 Apr. 13, 2023

Related U.S. Application Data

(60) Provisional application No. 63/254,339, filed on Oct. 11, 2021.

(51) Int. Cl.
*A61B 34/10* (2016.01)
*A61B 34/20* (2016.01)
(Continued)

(52) U.S. Cl.
CPC .............. *A61B 34/10* (2016.02); *A61B 34/20* (2016.02); *A61B 90/37* (2016.02); *G06T 7/0012* (2013.01);
(Continued)

(58) Field of Classification Search
None
See application file for complete search history.

(56) References Cited

U.S. PATENT DOCUMENTS

| | | | |
|---|---|---|---|
| 8,199,988 B2 | 6/2012 | Marshall et al. | |
| 9,336,336 B2 | 5/2016 | Deichmann et al. | |

(Continued)

FOREIGN PATENT DOCUMENTS

| | | | |
|---|---|---|---|
| CN | 111160326 A | 5/2020 | |
| CN | 112733579 A | 4/2021 | |

(Continued)

OTHER PUBLICATIONS

Parks, Connie L., et al., "Automated Facial Recognition of Computed Tomography-Derived Facial Images: Patient Privacy Implications", J Digit Imaging (2017) 30:204-214, published online Dec. 26, 2016.

(Continued)

*Primary Examiner* — Jeffrey J Chow
(74) *Attorney, Agent, or Firm* — Jeffrey Schox; Diana Lin

(57) ABSTRACT

The disclosure relates to a method including receiving a first set of images, the images being scans from one or more medical instruments; creating a patient-specific image reconstructed model based on the first set of images; defining mapping points on the reconstructed model; receiving a second set of images; defining patient recognition mapping points on the second set of images; overlaying the reconstructed model and the second set of images based on the mapping points and the recognition mapping points; and displaying the overlaid model aligned with the second set of images.

24 Claims, 14 Drawing Sheets

(51) Int. Cl.

| | |
|---|---|
| *A61B 90/00* | (2016.01) |
| *G06T 3/14* | (2024.01) |
| *G06T 7/00* | (2017.01) |
| *G06T 19/00* | (2011.01) |
| *G06T 19/20* | (2011.01) |

(52) U.S. Cl.
CPC ... *A61B 2034/105* (2016.02); *A61B 2034/107* (2016.02); *A61B 2034/2055* (2016.02); *A61B 2090/373* (2016.02); *A61B 2090/374* (2016.02); *G06T 3/14* (2024.01); *G06T 19/006* (2013.01); *G06T 19/20* (2013.01); *G06T 2207/10081* (2013.01); *G06T 2207/10088* (2013.01); *G06T 2207/10116* (2013.01); *G06T 2207/20081* (2013.01); *G06T 2207/20092* (2013.01); *G06T 2207/30016* (2013.01)

(56) References Cited

U.S. PATENT DOCUMENTS

| | | | | |
|---|---|---|---|---|
| 10,037,820 | B2 * | 7/2018 | Wong | G16H 50/50 |
| 10,178,155 | B2 | 1/2019 | Avisar | |
| 10,945,807 | B2 | 3/2021 | Gibby et al. | |
| 11,004,271 | B2 | 5/2021 | Cvetko et al. | |
| 11,123,144 | B2 | 9/2021 | Bustan et al. | |
| 2007/0249911 | A1 * | 10/2007 | Simon | G16H 70/20 |
| | | | | 600/300 |
| 2010/0249573 | A1 | 9/2010 | Marks | |
| 2015/0018842 | A1 | 1/2015 | Rahimian et al. | |
| 2017/0148213 | A1 | 5/2017 | Thomas et al. | |
| 2017/0312031 | A1 * | 11/2017 | Amanatullah | A61B 34/10 |
| 2020/0342675 | A1 * | 10/2020 | Leuze | G06T 7/0012 |
| 2021/0022812 | A1 | 1/2021 | Tako et al. | |
| 2021/0027469 | A1 * | 1/2021 | Lo | G06T 19/20 |
| 2021/0045701 | A1 | 2/2021 | Unklesbay et al. | |
| 2022/0096853 | A1 * | 3/2022 | Bakalo | A61B 90/36 |
| 2022/0110684 | A1 * | 4/2022 | Mensink | A61B 34/20 |
| 2022/0395328 | A1 * | 12/2022 | Wang | A61B 90/37 |
| 2022/0409281 | A1 * | 12/2022 | Gormley | A61B 34/25 |
| 2023/0149087 | A1 * | 5/2023 | Chen | G06T 7/33 |
| | | | | 345/419 |
| 2024/0320935 | A1 * | 9/2024 | Pissarenko | A61B 34/25 |

FOREIGN PATENT DOCUMENTS

| | | |
|---|---|---|
| EP | 1624823 B1 | 8/2018 |
| KR | 102007316 B1 | 8/2019 |

OTHER PUBLICATIONS

Alexander, Tyler , et al., "System and Method for Surgical State Prediction", U.S. Appl. No. 18/766,177, filed Jul. 8, 2024.

Kawka, Michal , et al., "Intraoperative video analysis and machine learning models will change the future of surgical training", Intelligent Surgery, vol. 1, Jan. 2022, pp. 13-15.

Lam, Klye , et al., "Machine learning for technical skill assessment in surgery: a systematic review", npj Digital Medicine vol. 5, Article No. 24 (2022).

Luongo, Francisco , et al., "Deep learning-based computer vision to recognize and classify suturing gestures in robot-assisted surgery", Surgery. May 2021; 169(5):1240-1244. doi: 10.1016/j.surg.2020. 08.016. Epub Sep. 26, 2020. PMID: 32988620; PMCID: PMC7994208.

Park, Juyoun , et al., "Recognition and Prediction of Surgical Actions Based on Online Robotic Tool Detection", IEEE Robotics and Automation Letters, Feb. 2021, accepted Jan. 2021.

Shi, Chang , et al., "Recognition and Prediction of Surgical Gestures and Trajectories Using Transformer Models in Robot-Assisted Surgery", 2022 IEEE/RSJ International Conference on Intelligent Robots and Systems (IROS), Oct. 23-27, 2022.

Vergouwen, Robin , "Improving surgeons' perform ance with AI", Incision Blog, Nov. 18, 2020, https://www.incision.care/blog/improving-surgeons-performance-with-ai.

* cited by examiner

204

304

404                                    402

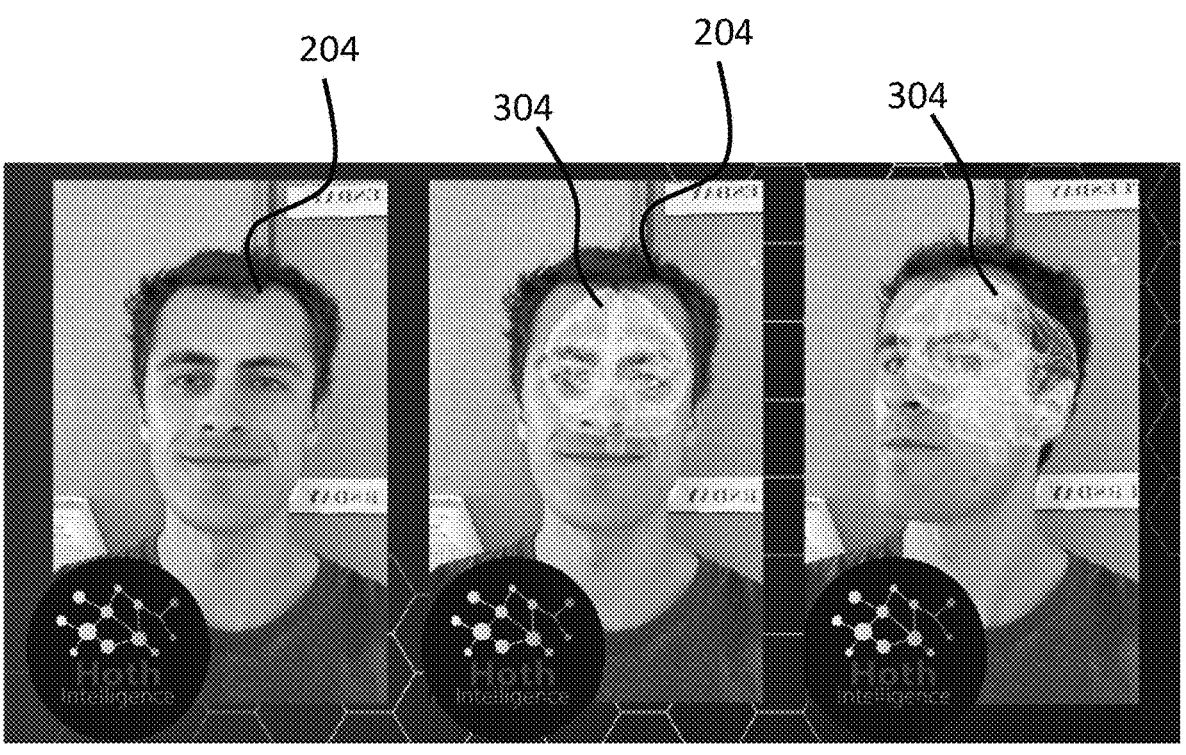
Fig. 8a          Fig. 8b          Fig. 8c

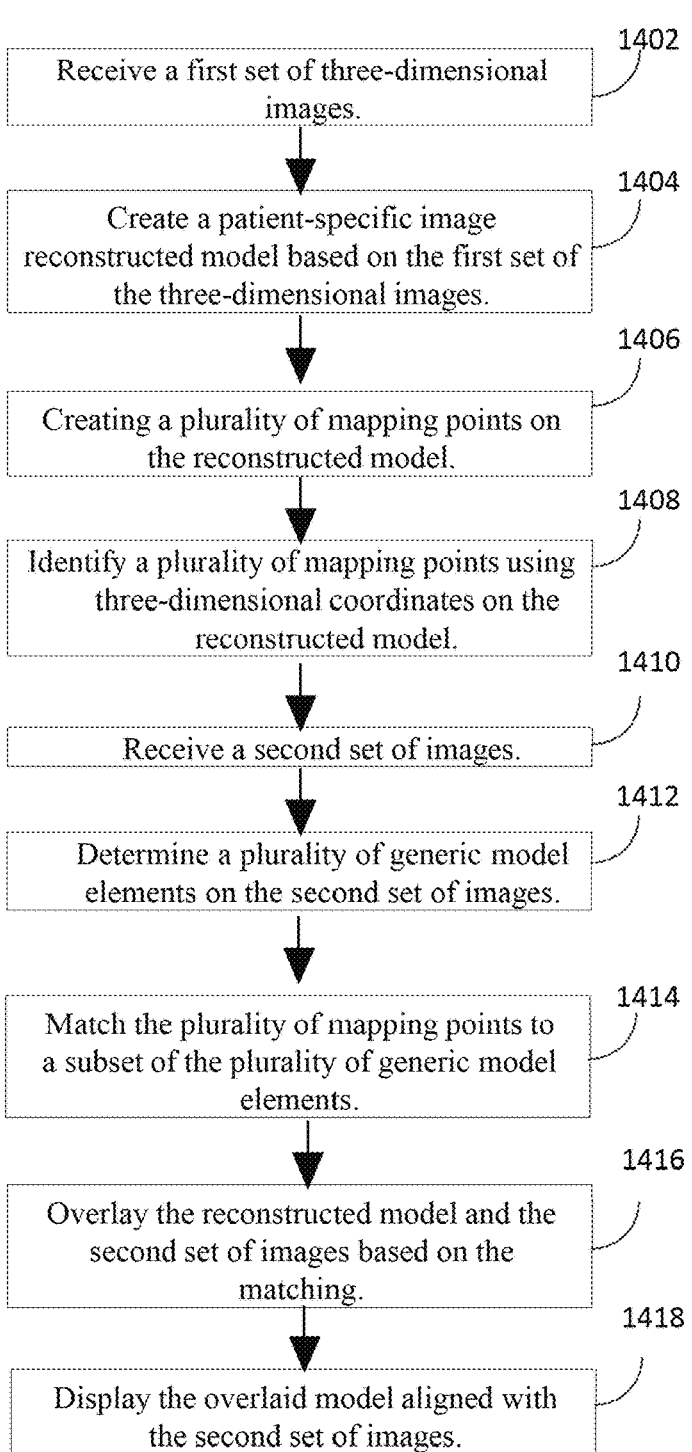

Receive a first set of three-dimensional images. — 1402

Create a patient-specific image reconstructed model based on the first set of the three-dimensional images. — 1404

Creating a plurality of mapping points on the reconstructed model. — 1406

Identify a plurality of mapping points using three-dimensional coordinates on the reconstructed model. — 1408

Receive a second set of images. — 1410

Determine a plurality of generic model elements on the second set of images. — 1412

Match the plurality of mapping points to a subset of the plurality of generic model elements. — 1414

Overlay the reconstructed model and the second set of images based on the matching. — 1416

Display the overlaid model aligned with the second set of images. — 1418

Fig. 14

METHOD FOR MEDICAL IMAGE RECONSTRUCTION

CROSS-REFERENCE TO RELATED APPLICATION(S)

This application claims the benefit of and priority to U.S. Provisional Application No. 63/254,339, filed on Oct. 11, 2021, entitled "SYSTEM AND METHOD FOR A TARGET RECONSTRUCTION PROCESS," which is hereby incorporated by reference in its entirety.

TECHNICAL FIELD

The present systems and methods are directed to creating a medical image reconstruction of a target patient on a device.

BACKGROUND

Currently, a registration process and a target reconstruction process for a facial reconstruction of a patient receiving treatment in the cranial region requires fiducial markers and a tapping or a tracing setting. A medical provider therefore spends significant time aligning or registering scans of the patient's anatomy—e.g., in the case of a cranial scan, the patients face, neck and head. However, the alignment or the registration processes fail when the patient's face moves. In addition, the equipment for the registration processes and the alignment can be quite expensive and take up a large amount of physical space. Therefore, there is a need to improve the registration processes for the medical image reconstruction of a patient to facilitate image-based treatment.

SUMMARY

In one aspect, the subject matter of this disclosure relates to a method including receiving a first set of images, the images being scans from one or more medical instruments; creating a patient-specific image reconstructed model based on the first set of images; defining mapping points on the reconstructed model; receiving a second set of images; defining patient recognition mapping points on the second set of images; overlaying the reconstructed model and the second set of images based on the mapping points and the recognition mapping points; and displaying the overlaid model aligned with the second set of images.

In another aspect, the subject matter of this disclosure relates to a method for creating a medical image reconstruction of a target patient on a display device. The method may include receiving, by a first processor, a first set of three-dimensional images, the first set of three-dimensional images being a set of scans from one or more medical imaging devices; creating, by the first processor, a patient-specific image reconstructed model based on the first set of three-dimensional images; identifying mapping points using three-dimensional coordinates on the reconstructed model; receiving, by a second processor, a second set of images, the second set of images captured by one or more cameras on the device; determining a plurality of generic model elements on the second set of images; matching the plurality of mapping points to a subset of the plurality of generic model elements; overlaying, by the second processor, the reconstructed model and the second set of images based on the matching; and displaying the overlaid model aligned with the second set of images.

In some embodiments, the first set of images may include images of at least one of a brain and skull. The one or more medical instruments may include at least one of computerized tomography scan, X-ray, and magnetic resonance imaging. The second set of images may include images of a head or a face of the target patient, and may be two or three-dimensional. The method may further include determining a device trajectory for a planned medical procedure using the overlaid model as a trajectory map. The method may further include receiving user input commands from a user of the display device, wherein the input commands direct a modification to the device trajectory. One end of the trajectory may be Kocher's point, the Kocher's point being a starting point of insertion of external ventricular drain, and in some instances the trajectory may guide a user of the display device when the user inserts a catheter into a target region of a brain of the patient. In some versions, the mapping points may include a facemask, which may be determined by a user of the display device and/or identified using a light detection and ranging (LIDAR) device. The generic model elements may include various anatomical features, such as an eye, an ear, a nose, a lip, forehead, an eyebrow and/or some portion or portions of such features. The method may further include tracking hands of a user as superimposed on the model as displayed on the display device to determine the generic model elements on the second set of images. The method may further include rotating the overlaid model and the second set of images in concert such that the mapping points remain aligned as the images are rotated on the display device.

In another aspect, the subject matter of this disclosure relates to a method for assisting a medical procedure being administered to a target patient. The method may include receiving, on an imaging and display device, a first set of images for a target area of the target patient captured prior to the medical procedure; receiving, on the imaging and display device, a second set of images including the target area of the target patient; determining a planned trajectory of a medical device as the medical procedure is administered based on the first and second sets of images; monitoring the medical procedure as the user operates the medical device according to the planned trajectory; and measuring an accuracy of the medical procedure.

In some embodiments, the medical procedure may include the insertion of a catheter into a brain of the target patient along the trajectory, and the accuracy may be based on whether or to what degree the catheter aligns with the trajectory. The method may further include providing feedback (e.g., a color coded display and/or a numeric indicator) of the accuracy to the user, thus allowing the user to adjust the trajectory during the procedure. The monitoring of the medical procedure may be performed by a sensor attaching to a catheter. The method may further include training the device to recognize the catheter. The accuracy of the medical procedure may be based, at least in part, on a variance between the planned trajectory and the monitored trajectory.

These and other objects, along with advantages and features of embodiments of the present invention herein disclosed, will become more apparent through reference to the following description, the figures, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIGS. 8*a-c* illustrate a rotation of the patient-specific image reconstructed model on the face of the patient, according to an embodiment of the present disclosure;

FIG. 14 illustrates a flowchart illustrates an overlay of a reconstructed model and a set of images based on matching points and generic model elements, according to an embodiment of the present disclosure.

DETAILED DESCRIPTION

Figure 1A:
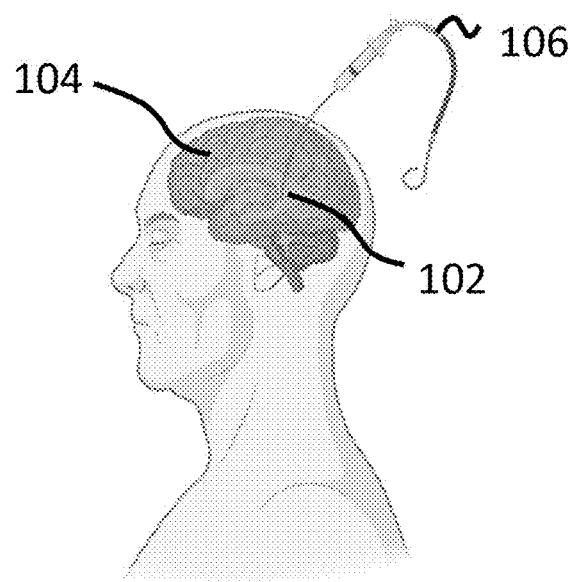
FIGS. 1*a* and 1*b* illustrate a demonstration of placement of external ventricular drain (EVD) in a patient's brain, according to an embodiment of the present disclosure.

It is contemplated that apparatuses, systems, methods, and processes of the claimed invention encompass variations and adaptations developed using information from the embodiments described herein. Adaptation and/or modification of the apparatuses, systems, methods, and processes described herein may be performed by those of ordinary skill in the relevant art.

It should be understood that the order of steps or order for performing certain actions is immaterial so long as the invention remains operable. Moreover, two or more steps or actions may be conducted simultaneously.

With reference to the drawings, aspects and embodiments of the invention will now be described in more detail. The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

The present disclosure describes methods and supporting systems that effectively and efficiently combine one or more anatomical images such as the combination of facial recognition images with cranial scans. For example, a patient's head may be scanned by a computerized tomography (CT) scan, which includes a series of X-ray images taken from different angles around the patient's head. The CT scan may include cross-sectional images or slices of bones, blood vessels, soft tissues, and brain inside the patient's head. After collecting the CT scan for the patient's head, components of the CT scan may be used as markers for a facial recognition imaging technique. The facial recognition imaging technique may create a facial recognition "mask" comprising points arranged about the patient's face. In addition, the CT scan may also include a plurality of mapping points corresponding to the points on the patient's face created by the facial recognition technique. A mapping process is then used to accurately map the plurality of mapping points on the CT scan to the points on the facial recognition mask.

In one embodiment, the image registration process may be either based on (1) facial recognition technology for head and neck procedures (as shown later in FIG. 4 herein) or (2) rapid scanning and 3D target-based reconstruction (as shown later in FIGS. 8*a*-8*c* herein) for any procedure in the healthcare field. The system and method for the registration process in the present disclosure may be used by medical providers as part of their existing operations and may provide an efficient and cost-effective method for the medical provider or the patient. The disclosed system and methods do not require an extensive setup and are able to integrate with the medical provider's workflow and use commercially-available scanning and display devices such as camera-enabled smartphones, virtual or augmented reality headsets, and the like. For example, a medical provider may have obtained CT scans before a brain surgery for a patient. With the integration of the facial recognition technique and the registration process based on the mapping of a plurality of mapping points from the CT scan to the points on the patient's face created by the facial recognition technique, the brain surgery performed by the medical provider may be more accurate.

In one embodiment, the present disclosure provides an alignment method and a registration process between a facial recognition process and scans such as CT scans. The facial recognition component in the facial recognition process is more robust and faster compared with conventional facial recognition processes. The alignment to the scans may be performed during the scans of a patient's face, so the scans continue even while the patient's head moves. Therefore, the alignment between the facial recognition process and scans compensates for and considers the movement of the patient. When a CT scan is used in the facial recognition process, the alignment method confirms that the CT scan remain aligned with the patient's head during the scans.

In some embodiments, the alignment method and the registration process may be used on various parts of a human body (or in some instances other animals) and addressing different anatomical features such as the face, head, neck, chest, arms, leg, abdomen or the like. Equipment used to implement the techniques described herein may be portable and the size of the equipment may be small. For example, the scanning device may be a handheld 3-dimensional scanning device and the scanning may provide real-time images of the target body part.

In one embodiment, commercially available tools such as ITK-SNAP and Unity Software can be used to implement certain scanning steps. These tools may be used to process scans such as CT scans or magnetic resonance imaging (MRI) scans. The images from the CT scans or the MRI scans may be presented as two-dimensional (2D) or three-dimensional (3D) images. In various embodiments of the invention, the 3D representation of the images of the CT scans and/or the MRI scans may further be integrated with other devices such as facial recognition devices, or augmented reality headsets, which may be familiar to the user, and thus may be easier or quicker to be integrated with the workflow of the medical providers. After the integration, a reconstruction of the patient's face based on the facial recognition techniques from the facial recognition devices and the 3-D representation of the images of the CT scans and the MRI scans may be formed, which may include providing an overlay of the facial recognition mask with points on the patient's face aligned with the plurality of mapping points on the CT scans or the MRI scans may also be performed.

In some embodiments, a camera rig setup may be used in the present disclosure. For example, a series of cameras can be used to take multiple pictures of an individual from different angles. These images can then be computationally "stitched" together to produce a 3D representation of the image. That 3D reconstruction can be used as a target (i.e., something that the software "looks for") when placing the 3D model of patient anatomy. The cameras used in the rig can be any sort of camera so long as they take images from different angles. These cameras can be mounted to comprise a single setup or can be entirely separate.

In one embodiment, the system and method of the present disclosure includes hand tracking and/or an instrumentation angle tracking. For example, during a medical procedure such as a brain surgery, a camera may track directional movements and/or the speed of the surgeon's hands to assist the surgeon in following a desired trajectory. In another example, the camera may track an instrumentation angle of one or more medical instruments relative to the facial recognition devices or the handheld CT scan device. Thus, during the integration of the facial recognition and the registration process, any misalignment between the patient's face and the instruments may be adjusted based on the tracking of the instrumentation angles.

In one embodiment, information from the facial recognition devices, images from the CT scan and/or the MM scan, information of the alignment process, and information of the overlap of the facial recognition mask with points on the patient's face with the plurality of mapping points on the CT scans or the MM scans may be transmitted to a server for processing. The server may be a local server, or a remote server provided by a third party. For example, information from the facial recognition devices such as the facial recognition mask annotated with points on the patient's face may be transmitted to a processor of a local server for an analysis of the locations of the mapping points on the image of the patient's face. The local server may further receive a plurality of mapping points on the CT scans or the MM scans. The processor may then analyze the received information and may further overlap the information on the image of the patient's face. After overlapping the information, the server may send the overlapped information to medical instruments being used by the medical provider to perform a medical procedure. The medical instruments can be, for example, a headset with an audio playback and/or visual display. The headset may be a device with cameras. The headset may further track faces and display information in the real world. The information provided to the medical provider may help the provider perform the medical procedure more effectively, quickly and/or accurately. In some embodiments, the headset on the medical provider may track hand movements of the medical provider such as, but not limited to, hand movement, arm angle, or instrumentation angle.

In one embodiment, the methods and the systems of the present disclosure may include optimization of the hand movement tracking, instrumentation angle tracking, arm tracking relative to the movement of the patient's face. For example, when a camera detects hand movement by one degree, the equipment can adjust the angle of the equipment accordingly based on optimization data. The optimization may be based on the facial recognition mask created from the face recognition devices and the mapping points from the images of the CT scan or the MRI scan, so that the equipment may also be aligned seamlessly and further reduce the procedure time and increase accuracy. In some embodiments, the optimization of the hand movement tracking may include tracking various points of a patient's hands, fingers, wrist, and both sides of the hands. In some instances, the patient may wear a tracking glove during the hand movement tracking process, so the hand movement tracking equipment may detect the hand movement. In some cases, the tracking system may receive sufficient information to track the patient's hands without the glove. The tracking system may also be used for medical procedures applied to other body parts of the patient.

In another case, a patient's face may rotate, for example, one degree, in which case the equipment adjusts the angle of the equipment based on the calculated optimization data. The optimization data may be based on the alignment of the facial recognition mask created from the face recognition devices and the mapping points from the images of the CT scan or the MRI scan. This allows the medical procedure to continue even after the patient's face moves while maintaining the alignment of the scan data and the facial recognition mask.

In one embodiment, a recognition algorithm may use images from the CT scan or the MRI scan as a target for the recognition algorithm. As discussed earlier, the target may be, but not limited to, face, neck, arm, chest, legs, or other anatomical regions of a patient.

In one embodiment, the combination of the anatomical recognition techniques and CT/MRI scans involves using a recognition mask of the patient target area that overlaps with mapping points of the CT scan or the MM scan. For example, for brain surgery, the target area is the head of the patient, and the recognition algorithm creates a recognition mask based on the CT scan of the patient's head. The surgeon's headset may then capture images of the patient's head just prior to and/or during the brain surgery and create a plurality of mapping points on the images, which may then further overlap the mapping points of the recognition mask with the mapping points of the images from the headset of the medical provider. By using this method, the medical procedure is more accurate and saves time for the medical provider.

In some embodiments, an overall registration process may include both a facial recognition technique and a handheld scanning technique. During the overlay process discussed above, the headset is registered to a particular patient, so that the headset knows where to place the CT scan or the MM scan relative to the mapping. For example, the headset recognizes a patient's face based on a facial scan and superimposes the image of the patient's brain on the patient's face, creating a composite image of the medical scan images and the facial recognition image from the scanning device.

In some embodiments in which a handheld scanner is used, the scanner captures images of the patient and then loads the captured images into the headset. The headset looks for the specific surface of the captured images on the patient and then superimposes the model on the surface of the patient based on the mapping points.

Figure 1B:
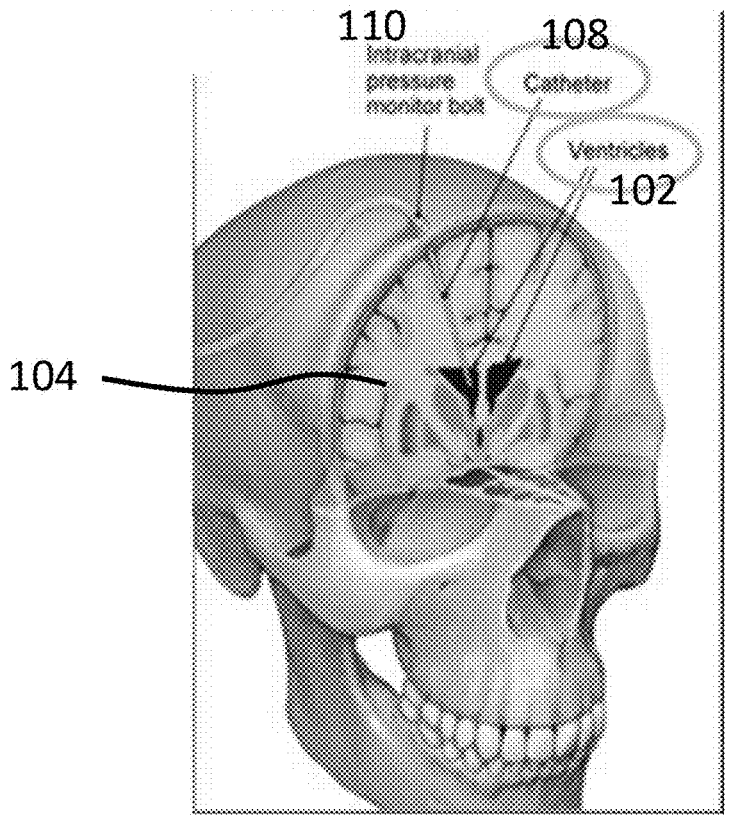

FIGS. 1a and 1b illustrate the placement of external ventricular drain (EVD) in a patient's brain, according to an embodiment of the present disclosure. More specifically, the ventricles 102 in the patient's brain 104 is shown, and the external ventricular drain 106 is connected to the ventricles 102 during an operation. For example, the external ventricular drain 106 may be used when a medical provider is placing an external ventricular drain in the patient. The external ventricular drain 106 may include a catheter 108 and an intracranial pressure monitor bolt 110 as shown in FIG. 1b. The catheter 108 may be used to drain cerebrospinal fluid (CSF) from the ventricles 102 of the patient to help relieve the intracranial pressure. The intracranial pressure monitor bolt 110 may be used to measure or monitor the intracranial pressure. The intracranial pressure monitor bolt 110 may be a small and hollow tube, which is the catheter 108, into the fluid-filled space, which is ventricle 102, in the brain 104. In some embodiments, the intracranial pressure monitor bolt 110 may be placed through the skull into the space between the skull and the brain 104.

Figure 2:
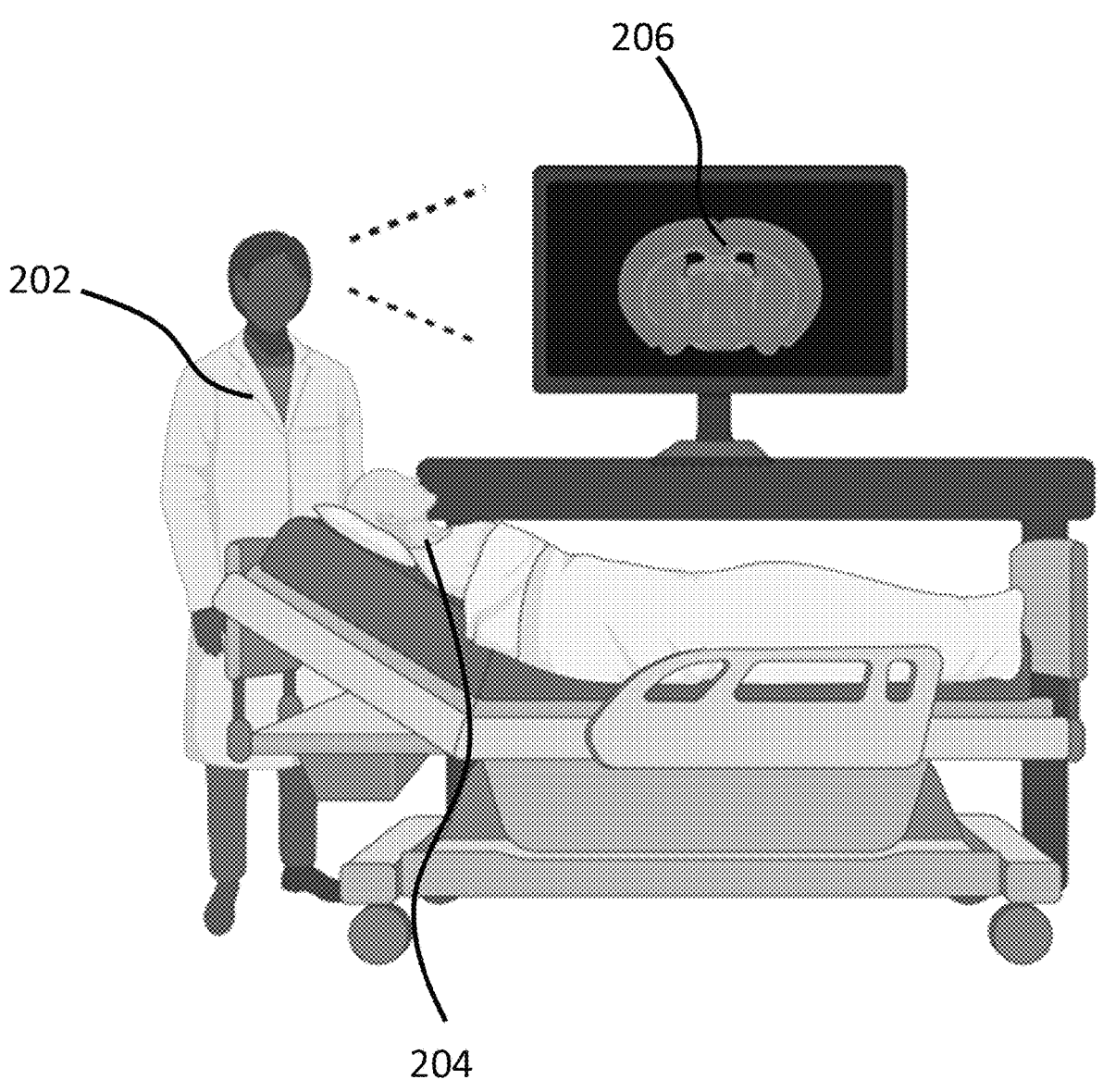
FIG. 2 illustrates an exemplary image overlay system, according to an embodiment of the present disclosure.

Referring to FIG. 2, an exemplary image overlay system is shown, according to an embodiment of the present disclosure. In FIG. 2, a medical provider 202 uses an image overlap system on a patient's image 206 of a patient 204 presented on the display device. The image overlay system may use the method described above to register the brain images from one or more medical imaging devices. The medical imaging devices may include computer tomography (CT) scan, X-ray, or magnetic resonance imaging (MRI) scan, and then display the patient's image 206 on the display while the medical procedure is being performed. In certain embodiments, the patient's image 206 may be a set of three-dimensional images taken by one or more of the medical imaging devices. The set of three-dimensional images may include, but are not limited to, brain, skull, or any body parts of the patient 204. The set of three-dimensional images may later be used to create a patient-specific image reconstructed model 304 in FIG. 3.

Figure 3:
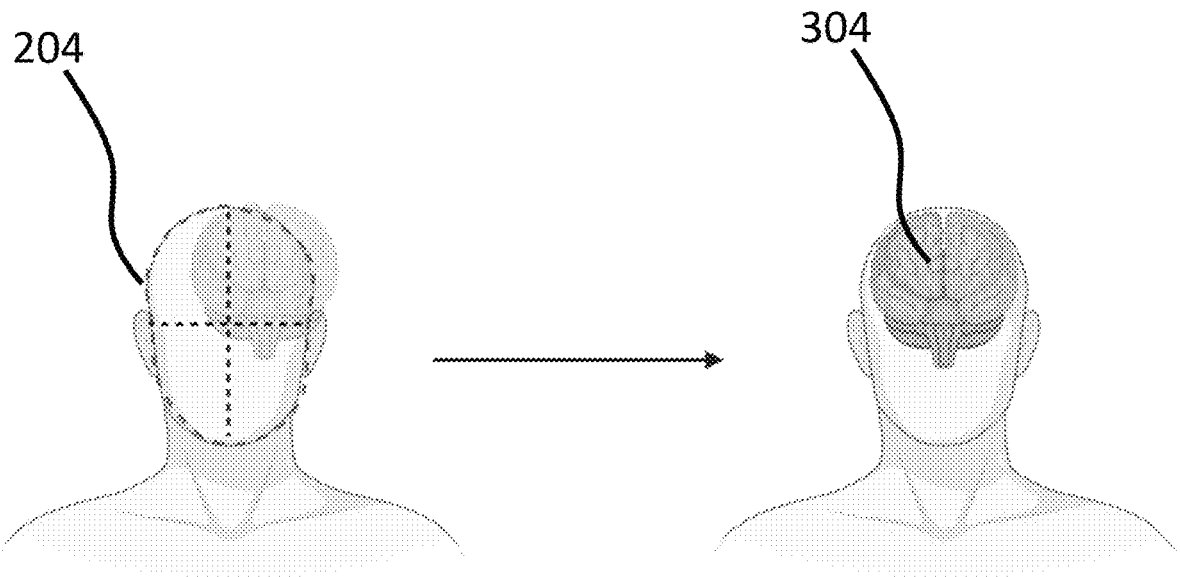
FIG. 3 illustrates a patient-specific image reconstructed model, according to an embodiment of the present disclosure.

In FIG. 3, a patient-specific image reconstructed model 304 is shown, according to an embodiment of the present disclosure. The patient-specific image reconstructed model 304 may be used to align with the an image of the patient 204. For example, by using the image overlay system discussed in the present disclosure, when the patient 204 moves their head, the image overlay system aligns the patient-specific image reconstructed model 304 with the patient's head using techniques described below and with reference to FIGS. 4-7.

Figure 4:
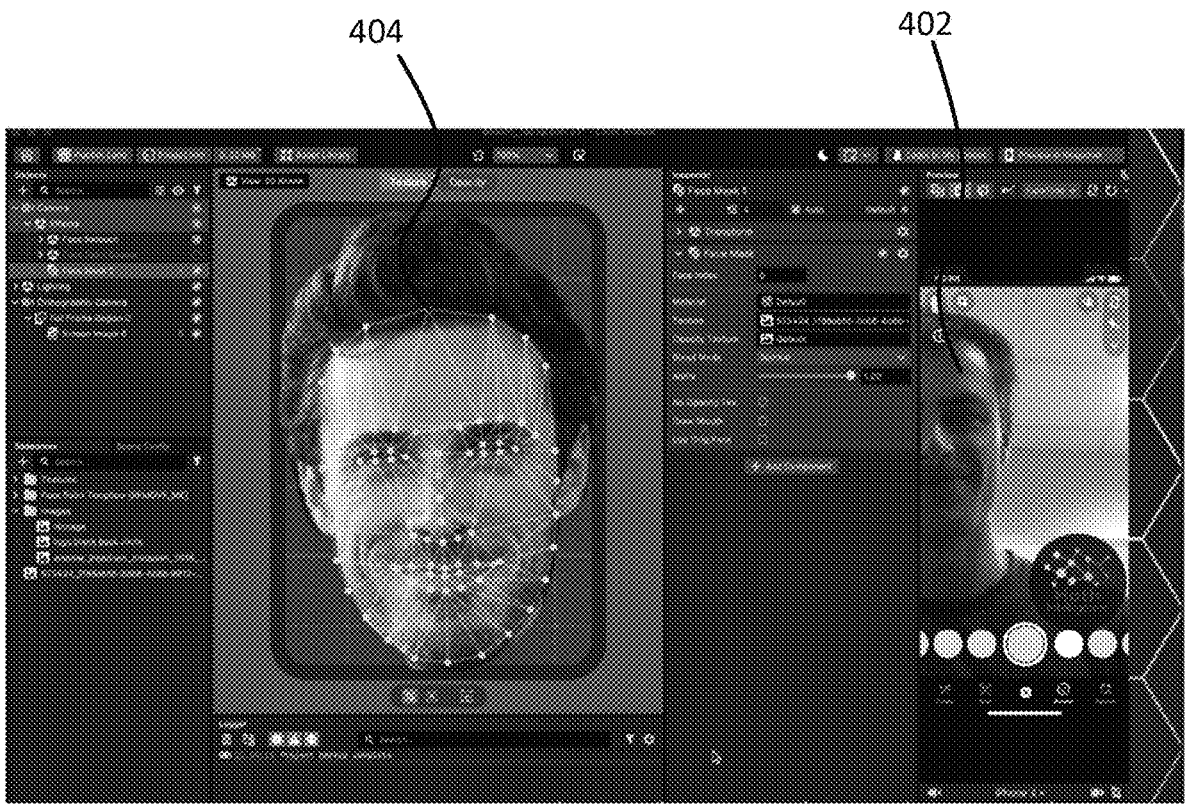
FIG. 4 illustrates a facial recognition system to detect and recognize a patient's face, according to an embodiment of the present disclosure.

In FIG. 4, the patient's face 402 is detected and recognized in the facial recognition system, according to an embodiment of the present disclosure. The facial recognition system may monitor location of the patient's face 402 and align the patient's face 402 to a center defined in the face recognition system, which then provides a facial recognition mask 404 on the patient's face 402 for the image overlay system. The facial recognition system may use a camera to monitor the location of the patient's face 402. The camera of the facial recognition system may be on the device belong to the medical provider, e.g., a headset or a holo lens.

In one embodiment, the set of three-dimensional images taken earlier by the medical imaging devices in FIG. 2 may be identified with mapping points using three-dimensional coordinates on the patient-specific image reconstructed model 304. For example, the facial recognition mask 404 in FIG. 4 may have a set of mask points from forehead to jaw vertically. In some embodiments, the facial recognition mask 404 may have another set of mask points and from right ear to the left ear horizontally.

Figure 5:
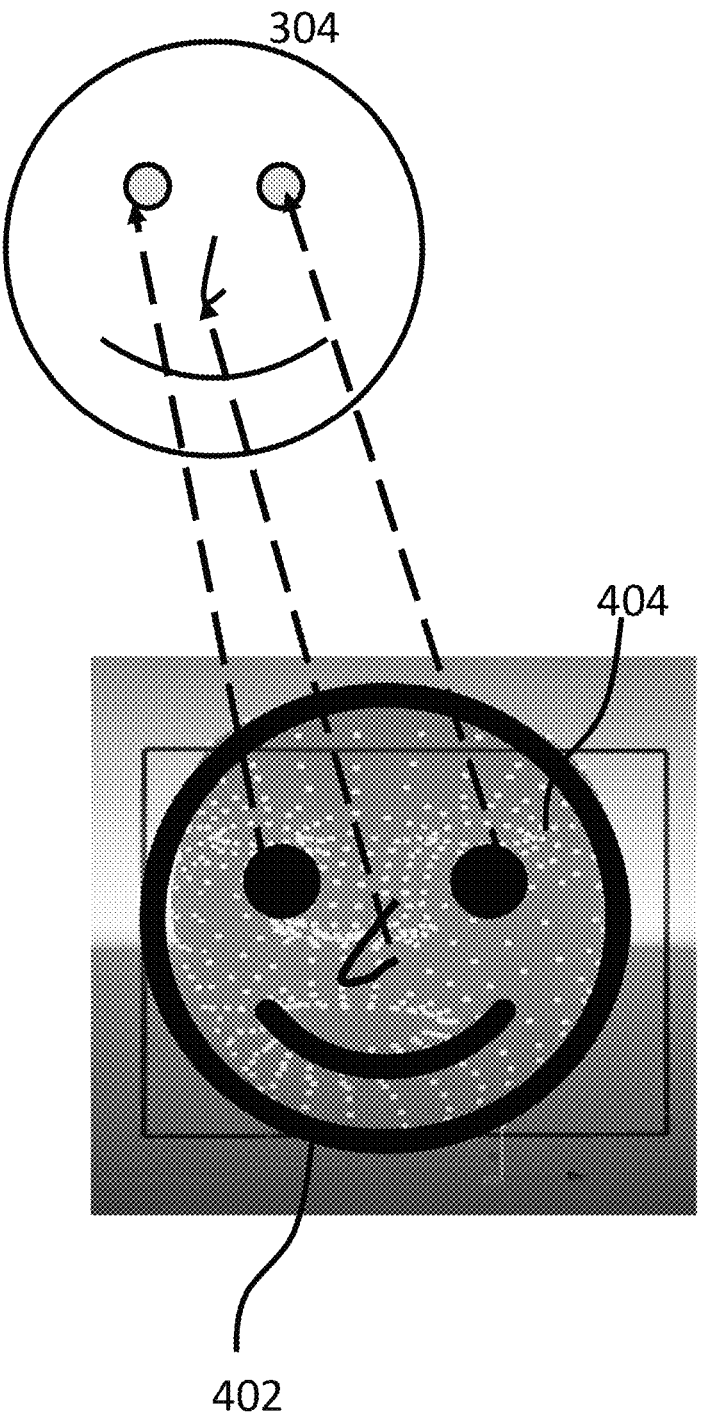
FIG. 5 illustrates a schematic view of aligning the facial recognition mask on a face with the patient-specific image reconstructed model and generic model elements, according to an embodiment of the present disclosure.

FIG. 5 shows a schematic view of aligning the facial recognition mask 404 on a face with the patient-specific image reconstructed model 304 and generic model elements, according to an embodiment of the present disclosure.

In one embodiment, as discussed above, the facial recognition mask 404 may include mapping points identified using three-dimensional coordinates on the patient-specific image reconstructed model 304. After the camera captures images of the patient's face, the generic model elements on the patient's face may be identified by the image overlay system. The generic model elements may include at least, but are not limited to, one or a portion of an eye, an ear, a nose, a lip, forehead, and an eyebrow of the patient 204. After identifying the generic model elements of the patient 204, the mapping points on the patient-specific image reconstructed model 304 may be mapped to the patient's face based on the identified generic model elements. For example, if the identified generic model element is a right eye of the patient's face, then the mapping points related to the right eye on the patient-specific image reconstructed model 304 may be used to align the right eye on the patient-specific image reconstructed model 304 to the right eye of the patient's face. After identifying several generic model elements and then further overlaying each of generic model elements of the patient-specific image reconstructed model 304 to the generic model elements on patient's face, the patient-specific image reconstructed model 304 is overlaid on the image of the patient's face. In some embodiments, an accuracy of the overlay may be calculated. In some embodiments, the accuracy may be presented as a score or numerical values.

Figure 6:
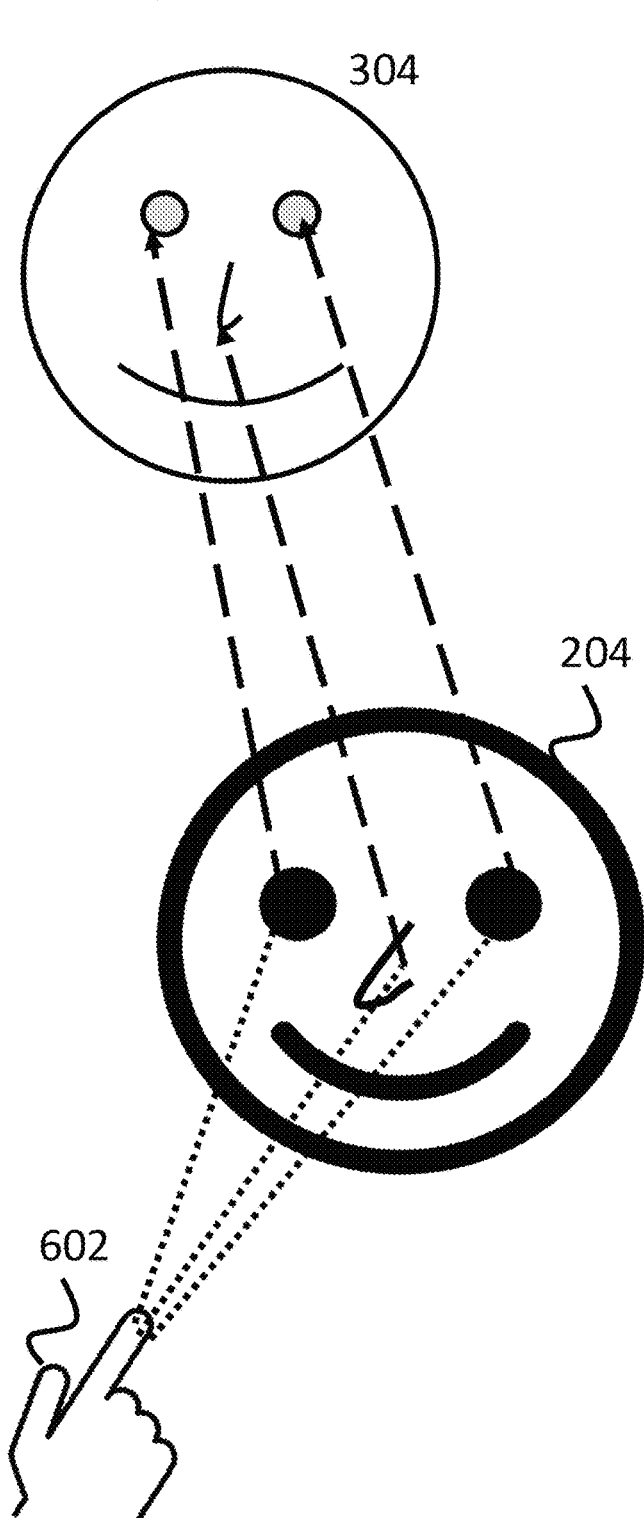
FIG. 6 illustrates a schematic view of aligning the patient's face with the patient-specific image reconstructed model by a user of the device, according to an embodiment of the present disclosure.

FIG. 6 shows a schematic view of aligning the patient's face with the patient-specific image reconstructed model 304 by a user of the device, according to an embodiment of the present disclosure.

In one embodiment, the users of the device, such as a holo lens or a headset, may use touch point registration. The touch point registration allows the users to use their hands 602 to identify positions of generic model elements. For example, a medical provider may use fingers to point out the positions of right eye, left eye, nose on the face of the patient 204 using their headset or the holo lens. The device may then locate the positions of these generic model elements and further overlay the patient-specific image reconstructed model 304 on the image of the face of the patient 204 using these positions. The medical provider or the users may also decide if more generic model elements are needed to accurately overlay the patient-specific image reconstructed model 304 on the face of the patient 204. In some embodiments, an accuracy of the overlay may also be calculated by the device. The accuracy of the overlay may be sent to a remote server for analysis and the user of the device may be able to access the analysis. In some embodiments, the accuracy may be presented as a score or numerical values.

Figure 7:
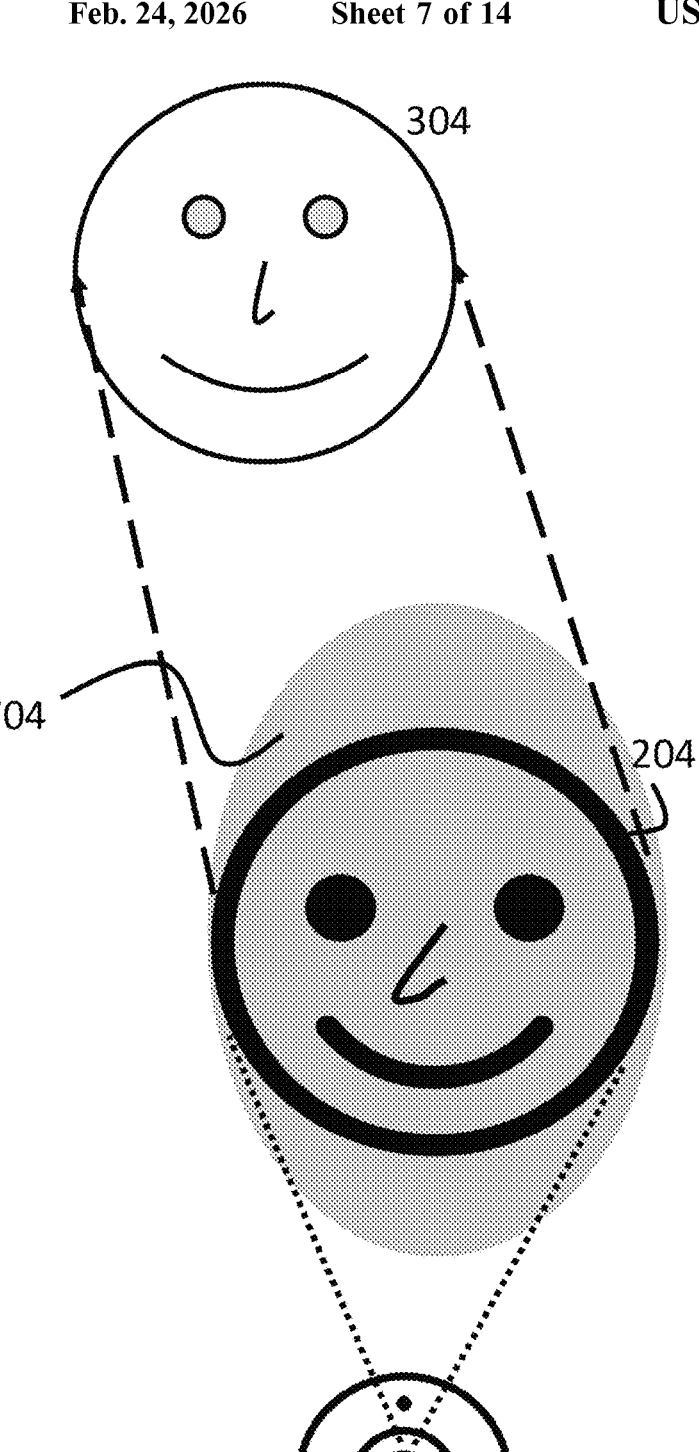
FIG. 7 illustrates a schematic view of aligning the patient's face with the patient-specific image reconstructed model by a light detection and ranging (LIDAR), according to an embodiment of the present disclosure.

FIG. 7 shows a schematic view of aligning the patient's face with the patient-specific image reconstructed model 304 by a light detection and ranging (LIDAR) 702, according to an embodiment of the present disclosure.

In one embodiment, the LIDAR 702 may scan the face of the patient 204 and the scan area 704 may cover the whole face. After scanning, positions of the generic model elements on the face of the patient 204 may be located. For example, the detection from the LIDAR may identify the positions of right eye, left eye, nose on the face of the patient 204. The patient-specific image reconstructed model 304 may then use these identified positions to overlay on the image of the face of the patient 204. In some embodiments, an accuracy of the overlay between the patient-specific image reconstructed model 304 and the face of the patient 204 may also be calculated. The accuracy of the overlay may be sent to a remote server for analysis and users of the system may be able to access the analysis. In some embodiments, the accuracy may be presented as a score or any numerical values.

FIGS. 8a-c show a rotation of the patient-specific image reconstructed model 304 on the face of the patient 204, according to an embodiment of the present disclosure.

In one embodiments, the patient-specific image reconstructed model 304, such as a brain model, may be overlayed with the image of the face of the patient 204 in the display based on the identified positions of the generic model elements on the face of the patient 204. The methods to overlay the patient-specific image reconstructed model 304 with the face of the patient 204 are discussed above in FIGS. 5-7. The generic model elements on the patient 304 may be identified in real-time such that when the patient 204 moves, the image overlay system may detect the changes and adjust the rotation or position of the patient-specific image reconstructed model 304 to overlay on the patient 204, thus maintaining the alignment. For example, when the patient 204 rotates his/her head to the right as shown in FIG. 8c, the brain model adjusts its rotation to the right accordingly.

Figure 9A:
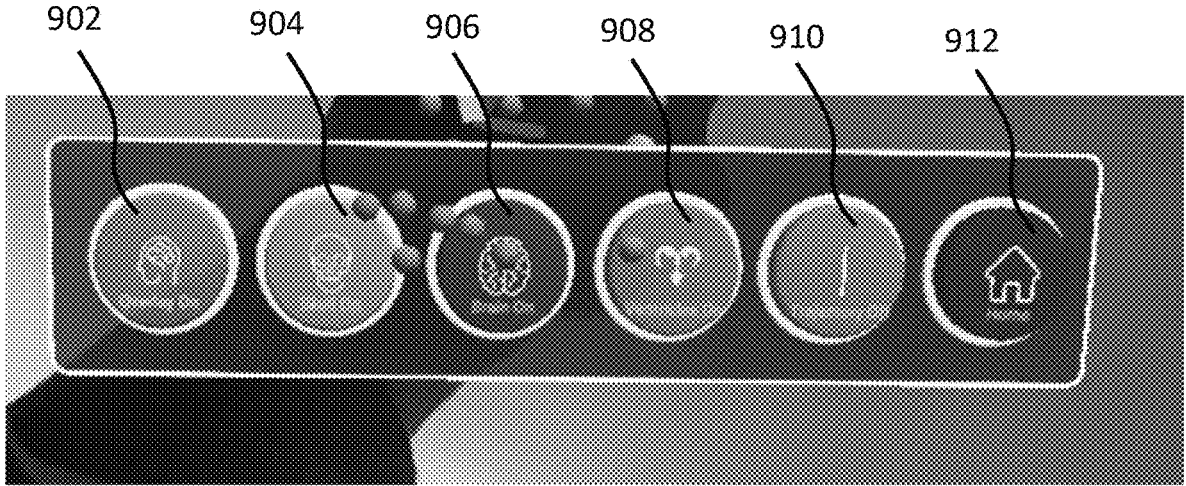
FIGS. 9*a* and 9*b* illustrate different functions on the image overlay system, according to an embodiment of the present disclosure.
Figure 9B:
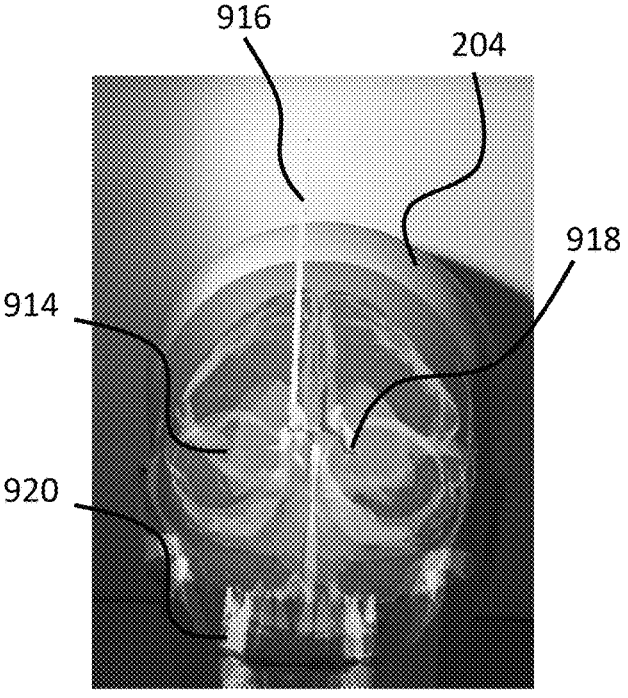

FIGS. 9a and 9b show different functions on the image overlay system, according to an embodiment of the present disclosure.

In one embodiment as illustrated in FIG. 9a, the image overlay system includes display controls such as overlay on/off 902, skull on/off 904, brain on/off 906, ventricles on/off 908, trajectory on/off 910, and home button 912. The overlay on/off 902 control indicates whether the patient-specific image reconstructed model 304 is overlaid on the image of the patient 204 or not, as shown in FIG. 9b. The skull on/off 904 control indicates whether a skull model 920 is overlaid on the image of the patient 204 or not, as shown in FIG. 9b. The brain on/off 906 control indicates whether a brain model 914 is overlaid on the image of the patient 204 or not, as shown in FIG. 9b. The ventricles on/off 908 control indicates whether a ventricle model 918 is overlaid on the image of the patient 204 or not, as shown in FIG. 9b.

In some implementations, the trajectory on/off 910 control indicates whether a trajectory 916 of the medical procedure is overlaid on the image of the patient 204 or not, as shown in FIG. 9b. In such cases, a user may follow the trajectory 916 to perform a medical procedure, using the image of the patient and one or more of the overlays as a guide. In some instances, an accuracy of the trajectory 916 being followed by the user as the procedure is performed on the patient may be calculated in real time and the user may receive an indication of the accuracy as feedback. User input commands such as modifications to the trajectory may be provided by a user via a user interface on the display device, in some cases as corrective instructions in response to the feedback. In particular instances, the trajectory may start from one end of the Kocher's point as the insertion point of an external ventricular drain (EVD). As such, the displayed trajectory and feedback may guide the user when inserting a catheter into a target region of a brain of the patient 204.

Figure 10A:
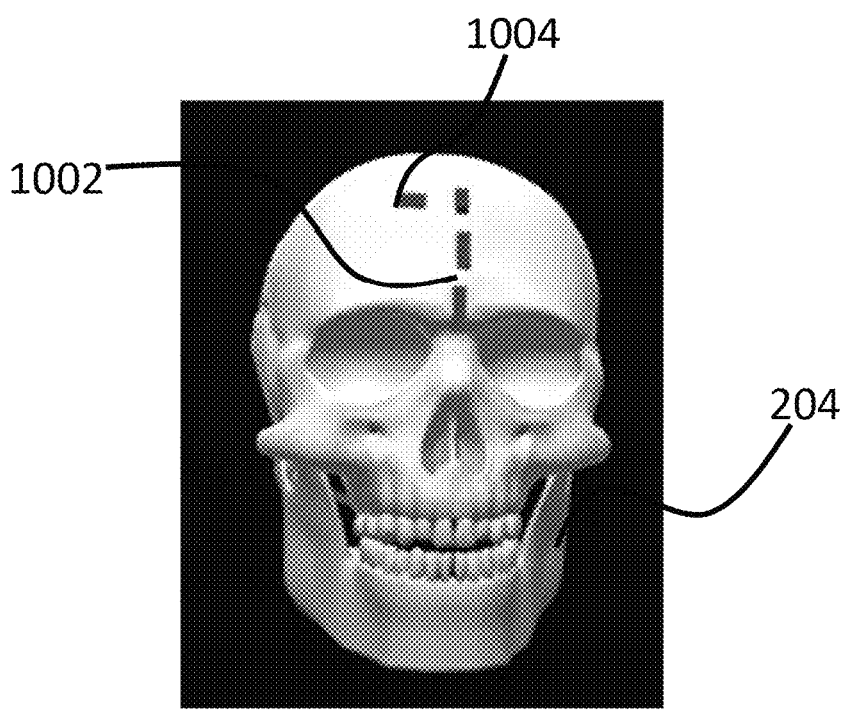
FIGS. 10*a* and 10*b* illustrate more detail of an exemplary procedure of an external ventricular drain (EVD) process, according to various embodiments of the present disclosure.
Figure 10B:
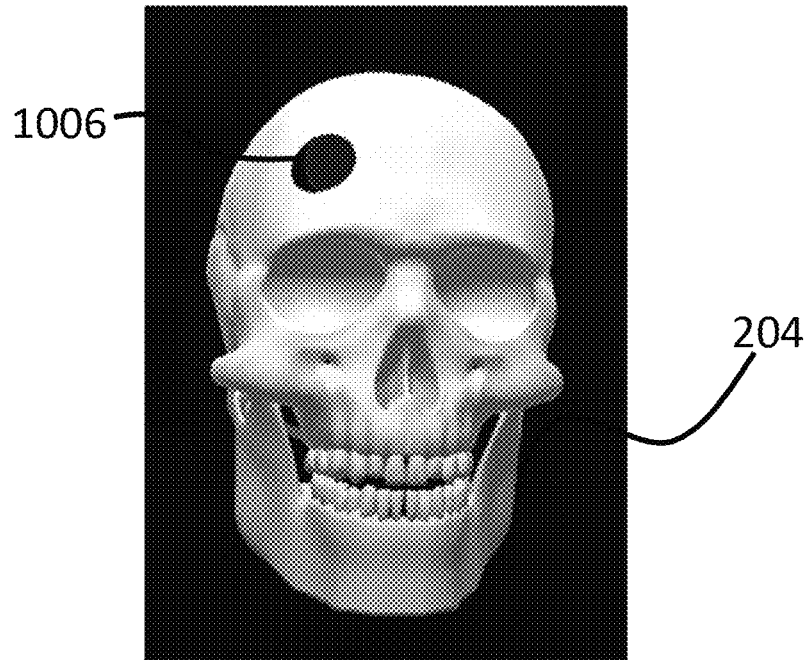

FIGS. 10a and 10b illustrate more details of an exemplary procedure of an external ventricular drain (EVD) process, according to various embodiments of the present disclosure.

In FIG. 10a, in order to locate a Kocher's point 1004 of the patient 204, first, the patient's head is rotated by 45 degrees. Second, starting from the bridge of the nose, a line 1002 is drawn upwards from the middle of the head. Third, starting from the bridge, a point 1004 is located along (e.g., 11 cm) and lateral (e.g., 3 cm) to the line 1002, and labeled as the Kocher's point 1004.

FIG. 10b illustrates the creation of a burr hole 1006. The procedure to create the burr hole 1006 starts from making a small incision at the labeled point, e.g., Kocher's point 1004, with a scalpel. A hand drill is then used to form a hole in the skull and stop drilling at the inner cortical bone to avoid contact with the brain, forming the burr hole 1006 on the skull.

Figure 11:
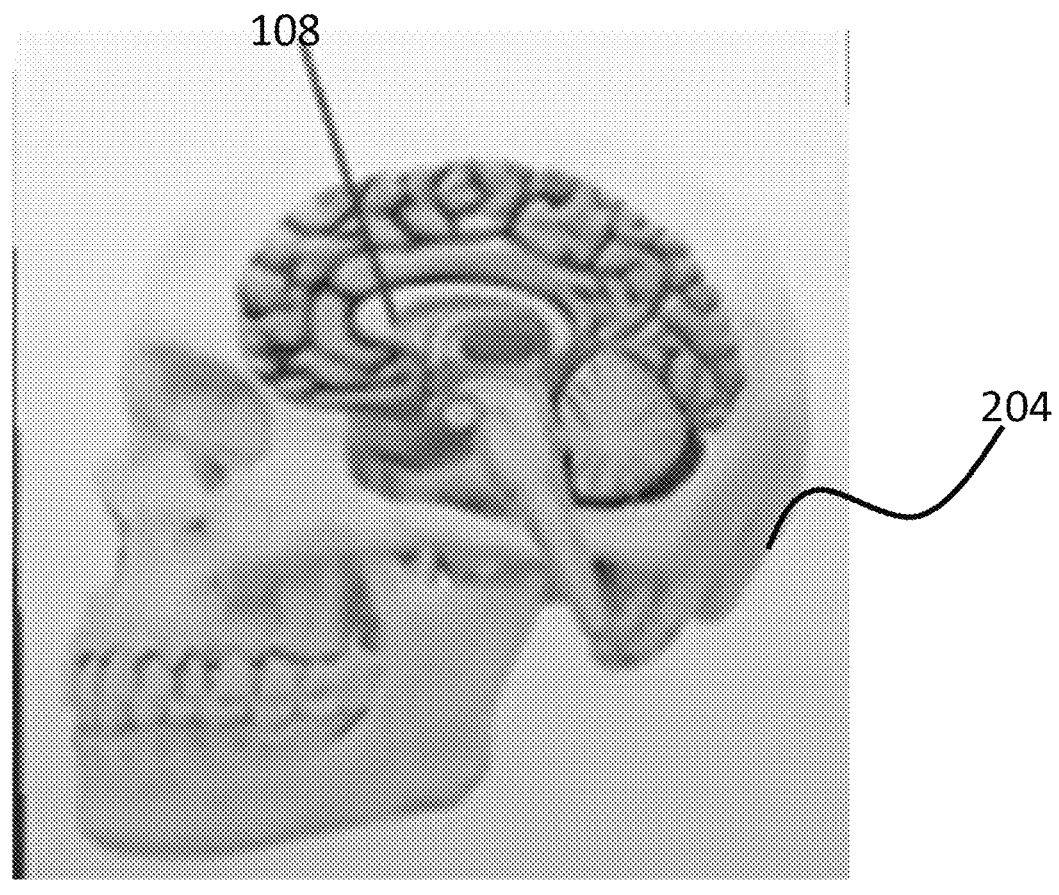
FIG. 11 illustrates a procedure of a placement of a catheter into the head of the patient, according to an embodiment of the present disclosure.

FIG. 11 shows a procedure of a placement of a catheter 108 into the head of the patient 204, according to an embodiment of the present disclosure.

With reference to FIGS. 10a and 10b discussed above, the burr hole 1006 is formed at the Kocher's point 1004 of the patient's head. The catheter 108 is positioned towards the ipsilateral medial canthus and ipsilateral tragus. By using markings on the catheter 108, the catheter 108 is inserted into the brain with a depth of 7 cm. After a successful insertion, a clear cerebrospinal fluid (CSF) fluid should pass through the catheter 108. In the last step, a collection tube is connected to the catheter 108. In some embodiments, the procedure of placement of the catheter 108 may be expand to dural drains, shunts, lumbar, ortho, or any other procedures.

Figure 12:
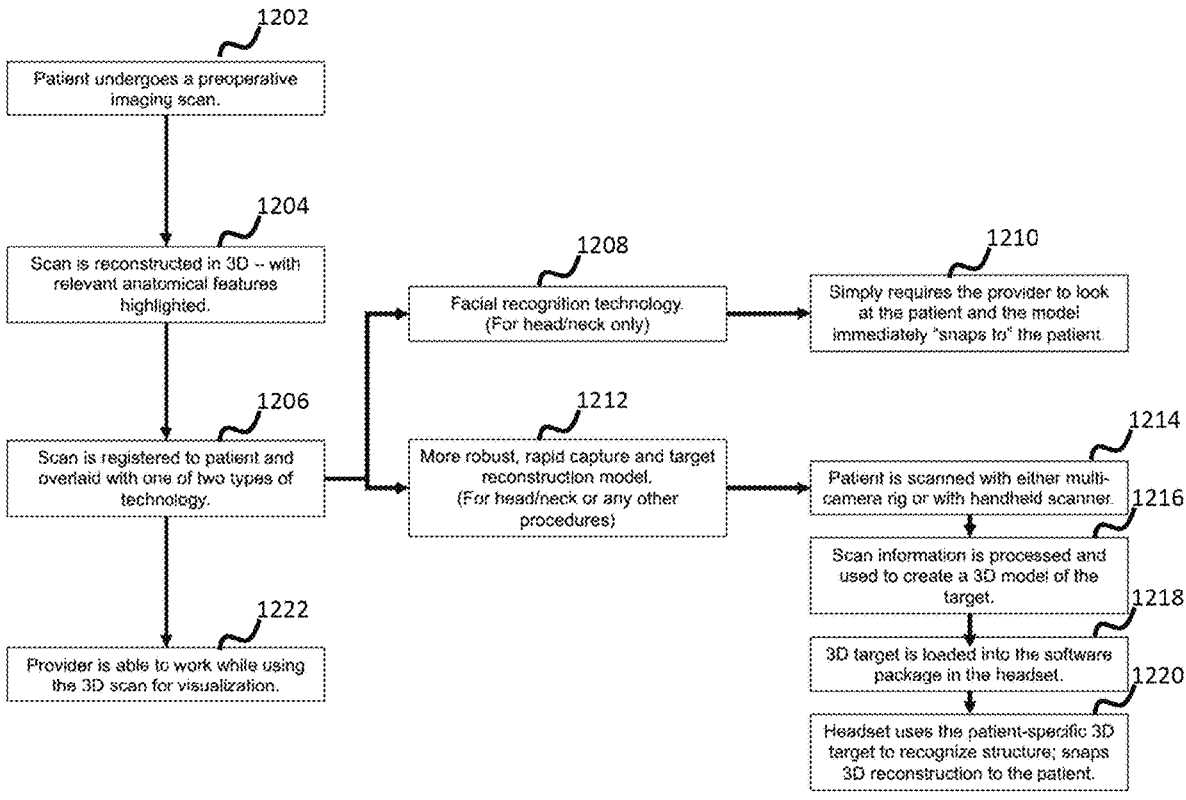
FIG. 12 illustrates a flowchart of the registration process of patient-specific models, according to various implementations of the invention.

FIG. 12 is a flowchart of the registration process of patient-specific models according to various implementations of the invention. At step 1202, a patient 204 undergoes a pre-operative imaging scan. For example, the pre-operative imaging scan may be a CT scan, a MRI scan, X-ray, or any scans discussed above. At step 1204, the pre-operative imaging scan is then reconstructed in a three-dimensional format. In some cases, anatomical features in the reconstruction of the pre-operative imaging scan may be highlighted. At step 1206, the three-dimensional (3D) pre-operative imaging scan is registered to the patient and overlaid using one or both of the techniques described below in steps 1208 and 1212.

At step 1208, a facial recognition technology is applied to positively identify the patient 204 as a particular individual. At step 1210, the medical provider looks at the patient while wearing a headset, and a model snaps to the image of patient. For example, if the model is a patient-specific image reconstructed model 304 such as a brain model, the brain model snaps to the image of the patient's head when the medical provider looks at the patient's head such that the model is accurately aligned with the image presented in the headset.

At step 1212, a target reconstruction model is retrieved from a model library, which may be used to create a robust model for various anatomical areas of the patient. At step 1214, the patient is scanned with either a multi-camera rig or with a handheld scanner, for example, the patient's chest may be scanned by a handheld CT scan device for chest and abdomen procedures.

At step 1216, scan data is processed and used to create a 3D model of the target patient area. For example, the scan information of the patient's chest in step 1214 may be processed and used to create a 3D chest model. At step 1218, the 3D target is provided to a software application and transmitted to a provider headset as described above. At step 1220, the headset of the medical provider uses the patient-specific 3D target to recognize structure and snaps the 3D target reconstruction to the display of the patient, and at step 1222, the medical provider can use the 3D scan for enhanced visualization and direction during the medical procedure.

Figure 13:
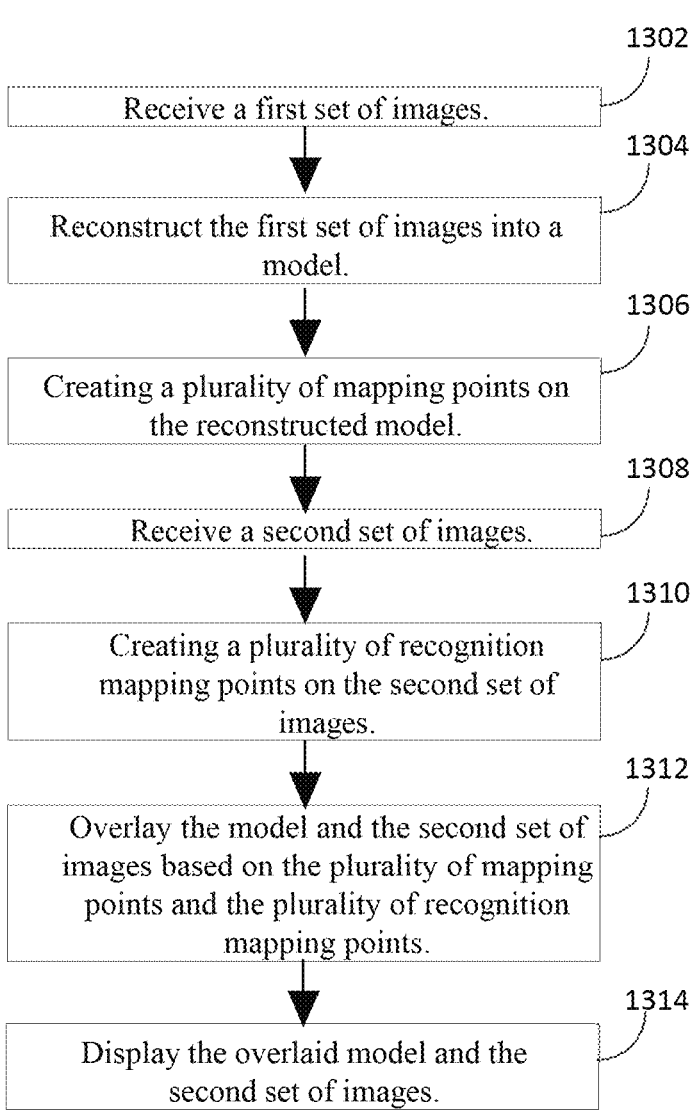
FIG. 13 illustrates a flowchart illustrates an image overlay method of overlaying images on a headset image as viewed by a medical provider, according to various implementations of the invention.

Referring to FIG. 13, a flowchart illustrates an image overlay method of overlaying images on a headset image as viewed by a medical provider. At step 1302, the processor receives a first set of images such as pre-operative CT or MRI scans. At step 1304, the first set of images are reconstructed into a model such as a brain model based on images of the patient's brain, which in some cases may highlight certain anatomical features in the brain model. At step 1306, mapping points are defined on the reconstructed model. At step 1308, a second set of images is received. The second set of images may be taken from a camera or cameras of the headset being used by the medical provider as they view the patient's head At step 1310, recognition mapping points on the second set of images are defined. For example, facial recognition mapping points may be created on the second sets of the images which shows the patient's head. At step 1312, the model and the second set of images based on the mapping points and the recognition mapping points are superimposed on each other such that they are anatomically aligned. For example, the second set of images showing the patient's head is overlayed with the brain model based on the mapping points and the recognition mapping points created earlier in steps 1306 and 1310. At step 1314, the overlaid model and the second set of images is displayed on the screen of the headset being used by the medical provider.

Referring to FIG. 14, a flowchart illustrates an overlay of a reconstructed model and a set of images based on matching points and generic model elements, according to an embodiment of the present disclosure. At step 1402, a first set of three-dimensional images such as scans from medical imaging devices is received. At step 1404, patient-specific image reconstructed model based on the first set of three-dimensional images is created. At step 1406, mapping points using three-dimensional coordinates on the reconstructed model are identified. At step 1408, mapping points using three-dimensional coordinates as a reference to the reconstructed model are identified. At step 1410, a second set of images captured by one or more cameras on the device is received by another processor.

At step 1412, a plurality of generic model elements are identified on the second set of images. At step 1414, the mapping points are anatomically matched to a subset of the generic model elements. At step 1416, the reconstructed model is overlaid with the second set of images based on the matched points such that the aligned images are displayed.

The techniques described herein can be implemented in digital electronic circuitry, or in computer hardware, firmware, software, or in combinations of them. The techniques can be implemented as a computer program product, i.e., a computer program tangibly embodied in an information carrier, e.g., in a machine-readable storage device or other non-transitory storage medium, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps of the techniques described herein can be performed by one or more programmable processors executing a computer program to perform functions of the invention by operating on input data and generating output. Method steps can also be performed by, and apparatus of the invention can be implemented as, special purpose logic circuitry, e.g., an FPGA (field programmable gate array) or an ASIC (application-specific integrated circuit). Modules can refer to portions of the computer program and/or the processor/special circuitry that implements that functionality.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

The techniques and system architecture described herein can be implemented in a distributed computing system that includes a back-end component, e.g., as a data server, and/or a middleware component, e.g., an application server, and/or a front-end component, e.g., a client computer having a graphical user interface and/or a Web browser through which a user can interact with an implementation of the invention, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet, and include both wired and wireless networks.

The computing system can include clients and servers. A client and server are generally remote from each other and typically interact over a communication network. The relationship of client and server arises by virtue of computer programs running on the respective computers and having a client-server relationship to each other.

It is to be understood that the above descriptions and illustrations are intended to be illustrative and not restrictive. It is to be understood that changes and variations may be made without departing from the spirit or scope of the following claims. Other embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventor did not consider such subject matter to be part of the disclosed inventive subject matter.

Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

Obviously, numerous modifications and variations are possible in light of the above teachings. It is therefore to be understood that within the scope of the appended claims, embodiments of the present disclosure may be practiced otherwise than as specifically described herein.

What is claimed is:

1. A method for creating a medical image reconstruction of a target patient on a display device, the method comprising:

receiving, by a first processor, a first set of three-dimensional images, the first set of three-dimensional images being a plurality of scans from one or more medical imaging devices;

creating, by the first processor, a patient-specific image reconstructed model based on the first set of three-dimensional images;

identifying a set of facial features from the reconstructed model;

based on positions of the set of facial features, extracting a virtual face mask from the reconstructed model;

identifying a plurality of mapping points using three-dimensional coordinates on the virtual face mask extracted from the reconstructed model;

receiving, by a second processor, a second set of images, the second set of images captured by one or more cameras on the display device;

determining a plurality of generic model elements in the second set of images;

matching the plurality of mapping points to a subset of the plurality of generic model elements;

overlaying, by the second processor, the reconstructed model and the second set of images based on the matching; and displaying the overlaid model aligned with the second set of images on the display device.

2. The method of claim 1, wherein the first set of images include images of at least one of a brain and skull.

3. The method of claim 1, wherein the one or more medical instruments include at least one of computerized tomography scan, X-ray, and magnetic resonance imaging.

4. The method of claim 1, wherein the second set of images include images of a head or a face of the target patient.

5. The method of claim 1 further comprising determining a device trajectory for a planned medical procedure on the overlaid model.

6. The method of claim 5, further comprising receiving user input commands from a user of the display device, wherein the input commands direct a modification to the device trajectory.

7. The method of claim 6, wherein one end of the device trajectory is at a Kocher's point, the Kocher's point being a starting point of insertion of external ventricular drain.

8. The method of claim 6, wherein the device trajectory guides a user of the display device when the user inserts a catheter into a target region of a brain of the target patient.

9. The method of claim 1, wherein the plurality of mapping points comprise mapping points extracted from the virtual face mask.

10. The method of claim 1, wherein the plurality of mapping points are determined by a user of the display device.

11. The method of claim 1, wherein the plurality of mapping points are identified using a light detection and ranging (LIDAR) device.

12. The method of claim 1, wherein the plurality of generic model elements include at least one or a portion of an eye, an ear, a nose, a lip, forehead, and an eyebrow.

13. The method of claim 1, further comprising tracking hands of a user of the display device to determine the plurality of the generic model elements on the second set of images.

14. The method of claim 1, wherein the second set of images are two-dimensional images.

15. The method of claim 1, further comprising rotating the overlaid model and the second set of images in concert such that the mapping points remain aligned as the images are rotated on the display device.

16. The method of claim 15 wherein the rotation is directed by a user command provided to the display device.

17. A method for assisting a medical procedure being administered to a target patient, the method comprising:

receiving, on an imaging and display device, a first set of images for a target area of the target patient captured prior to the medical procedure;

receiving, on the imaging and display device, a second set of images including the target area of the target patient;

creating a reconstructed model based on the first set of images;

identifying a set of facial features from the reconstructed model;

based on positions of the set of facial features, extracting a virtual face mask from the reconstructed model;

identifying a plurality of mapping points using three-dimensional coordinates on the virtual face mask;

based on a matching of the plurality of mapping points to features within the second set of images, overlaying the reconstructed model onto the second set of images;

determining a planned trajectory of a medical device as the medical procedure is administered based on the first and second sets of images;

16 monitoring the medical procedure as a user operates the medical device according to the planned trajectory; and measuring an accuracy of the medical procedure.

18. The method of claim 17, wherein the user inserts a catheter into a brain of the target patient along the planned trajectory.

19. The method of claim 18, wherein the accuracy is based on whether the catheter aligns with the planned trajectory.

20. The method of claim 17, further comprising providing feedback of the accuracy to the user.

21. The method of claim 20, wherein the feedback is provided to the user on the imaging and display device in the form of one or more of a color coded indicator and a numeric indicator.

22. The method of claim 17, wherein the monitoring of the medical procedure is performed by a sensor attaching to a catheter.

23. The method of claim 17, further comprising training the device to recognize the catheter.

24. The method of claim 17, wherein the accuracy of the medical procedure is based, at least in part, on a variance between the planned trajectory and a monitored trajectory.

* * * * *